United States Patent [19]

Sontag

[11] Patent Number: 5,236,443

[45] Date of Patent: Aug. 17, 1993

[54] SUTURING ASSEMBLY AND METHOD

[76] Inventor: Sidney Sontag, 7300 SW. 18th St., Plantation, Fla. 33317

[21] Appl. No.: 967,176

[22] Filed: Oct. 27, 1992

Related U.S. Application Data

[63] Continuation-in-part of Ser. No. 887,181, May 21, 1992, Pat. No. 5,180,385.

[51] Int. Cl.⁵ ............................................. A61B 17/00
[52] U.S. Cl. ..................................... 606/224; 606/223
[58] Field of Search ................................. 606/222-227

[56]  References Cited

U.S. PATENT DOCUMENTS

| | | | |
|---|---|---|---|
| 1,844,364 | 2/1932 | Lowrie | 606/223 |
| 3,212,502 | 10/1865 | Myers | 606/224 |
| 4,392,495 | 7/1983 | Bayers | 606/224 |
| 4,901,722 | 2/1990 | Noguchi | 606/224 |
| 4,932,962 | 6/1990 | Yoon | 606/224 |
| 4,966,143 | 10/1990 | Meinershager | 606/223 |

Primary Examiner—Stephen C. Pellegrino
Assistant Examiner—Gary Jackson
Attorney, Agent, or Firm—Connolly and Hutz

[57] ABSTRACT

A surgical suturing assembly and method of suturing are provided. The suturing assembly comprises a surgical needle having a pin within a casing or sheath having an aperture, wherein the pin of the needle is within the casing aperture. A suture is attached to the needle, casing or both. In use, a surgeon slides the pin of the needle, forcing the sharpened distal point of the needle to project through the distal opening of the casing. Once the distal portion of the needle/casing assembly penetrates the tissue, the sliding force is released or retracted which causes the needle to return to its original position, leaving an unsharpened point for further manipulation. The chance of needle-stick is thus greatly reduced.

7 Claims, 4 Drawing Sheets

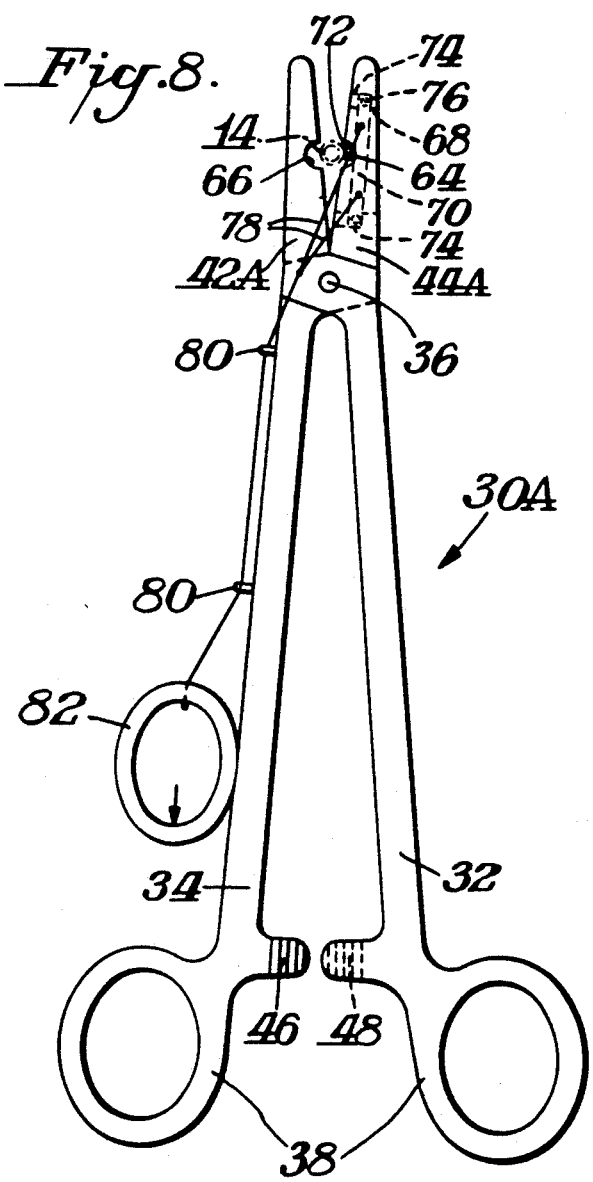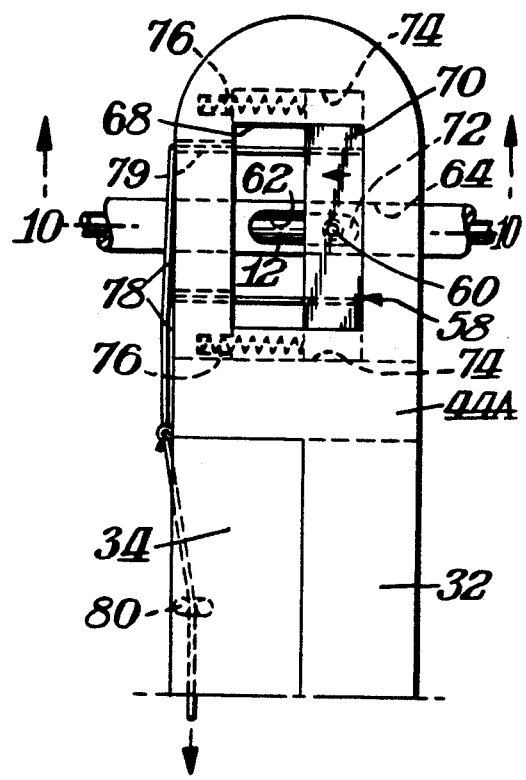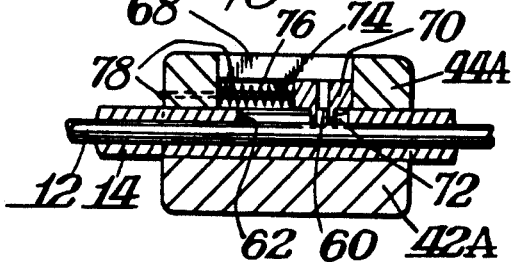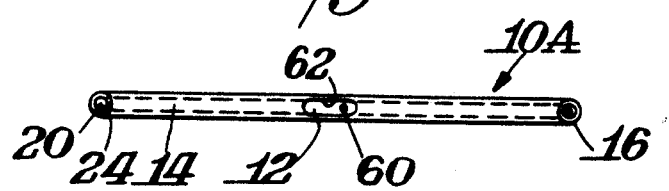

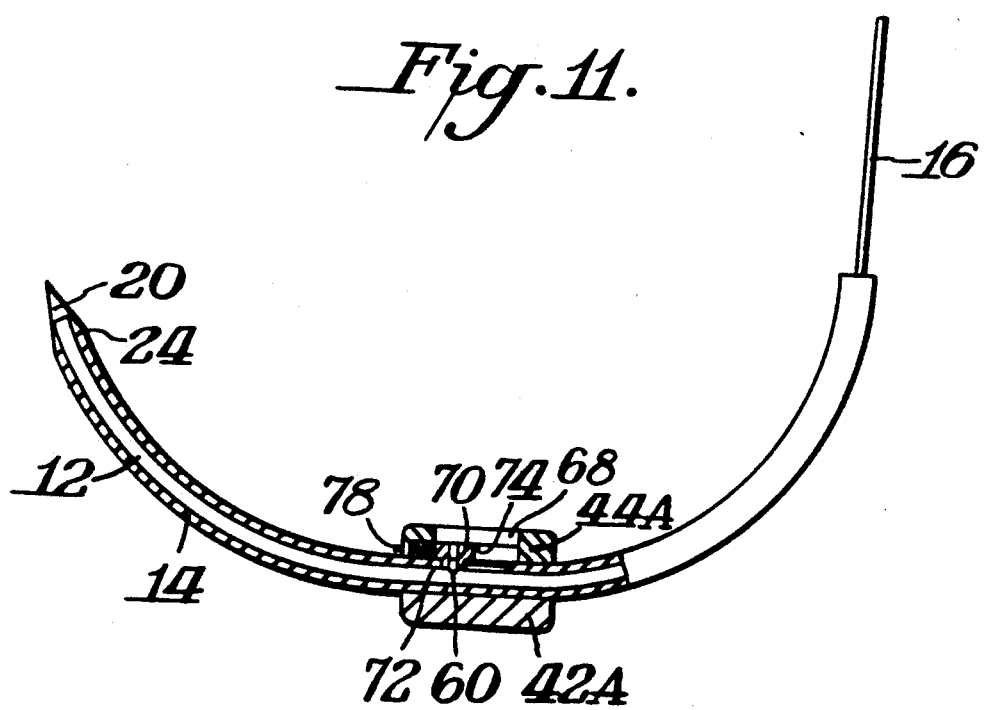

SUTURING ASSEMBLY AND METHOD

This is a continuation-in-part of Ser. No. 887,181, filed May 21, 1992 now U.S. Pat. No. 5,180,385.

BACKGROUND OF THE INVENTION

The present invention relates to a new suturing devices, the object of which is to avoid the common problem of "needle stick", i.e., the unintended puncturing of a surgeon's glove and skin with a suturing needle. Needle stick is a common problem in surgery and has resulted in the fatal transmission of the AIDS and hepatitis viruses. The growing prevalence of AIDS and hepatitis makes it imperative to develop surgical needles which will not expose the surgeon, nurses and other personnel who come in contact with the contaminated needle to an accidental puncture during suturing. Although the problem has been evident for some years, no surgical needles are available which meet this need. The present invention is designed to suture with reduced risk of needle stick.

SUMMARY OF THE INVENTION

The present invention involves a unique suturing assembly generally comprising:
a) a casing comprising
   i) an elongated hollow shaft having a generally longitudinal axis,
   ii) an aperture along a portion of the longitudinal axis, and
   iii) an opening terminating the casing at the distal end;
b) a surgical needle comprising
   i) a stem along a generally elongated longitudinal axis having either a hump along a portion thereof laterally offset from the longitudinal axis or a pin perpendicularly offset from the longitudinal axis, and
   ii) a sharpened distal point terminating the stem in one direction;
c) said surgical needle located within said casing whereby
   i) the longitudinal axis of said surgical needle and casing are disposed in a substantially coaxial relationship,
   ii) with the hump or pin of said surgical needle disposed within and protruding through the aperture of said casing,
   iii) the sharpened distal point of the said surgical needle being disposed proximal to the opening of the distal end of said casing at rest and capable of being projected through the said distal opening of said casing upon either the application of force to the said hump of said surgical needle or the application of a sliding force to the said pin, and
   iv) whereby the said surgical needle and said casing can be manipulated as a unit upon the application of manipulative force thereto; and
d) a suture having an end portion thereof inserted into and fixed to the said needle, casing or both.

The present invention also involves a unique suturing method comprising
I) grasping a suturing assembly generally comprising in a rest position
a) a casing comprising
   i) an elongated hollow shaft having a generally longitudinal axis,
   ii) an aperture along a portion of the longitudinal axis,
   iii) an opening terminating the casing at the distal end;
b) a surgical needle comprising
   i) a stem along a generally elongated longitudinal axis having either a hump along a portion thereof laterally offset from the longitudinal axis or a pin perpendicularly offset from the longitudinal axis, and
   ii) a sharpened distal point terminating the stem in one direction;
c) said surgical needle located within said casing whereby
   i) the longitudinal axis of said surgical needle and casing are disposed in a substantially coaxial relationship,
   ii) with the hump or pin of said surgical needle disposed within and protruding through the aperture of said casing, and
   iii) the sharpened distal point of the said surgical needle being disposed proximal to the opening of the distal end of said casing; and
d) a suture having an end portion thereof inserted into and fixed to the said needle, casing or both;
II) either (A) deforming the hump of the needle stem or (B) sliding the pine and needle stem in a distal direction, so as to extend the longitudinal length of the surgical needle within the casing until the sharpened distal point of the needle projects through the distal opening of the casing;
III) piercing the material to be sutured;
IV) releasing the deforming force upon the hump or retracting the sliding force on the pin of the needle so that the said surgical needle returns to the rest position; and
V) advancing the suturing assembly as a unit through the material to be sutured.

BRIEF DESCRIPTION OF THE DRAWINGS

FIG. 7 is a top plan view showing another suturing assembly of this invention;

FIG. 8 is a top plan view showing a needle holder top to be used with the suturing assembly shown in FIG. 7;

FIG. 9 is a fragmental right side elevational view of surgical pliers operatively engaged with the suturing assembly;

FIG. 10 is a cross-sectional view taken along line 10—10 of FIG. 9; and

FIG. 11 is a side elevational view partially in cross-section showing the surgical pliers engaged with and extending the surgical needle into its suturing position.

In the figures, the thickness is shown on an exaggerated scale.

DETAILED DESCRIPTION

Figure 1:
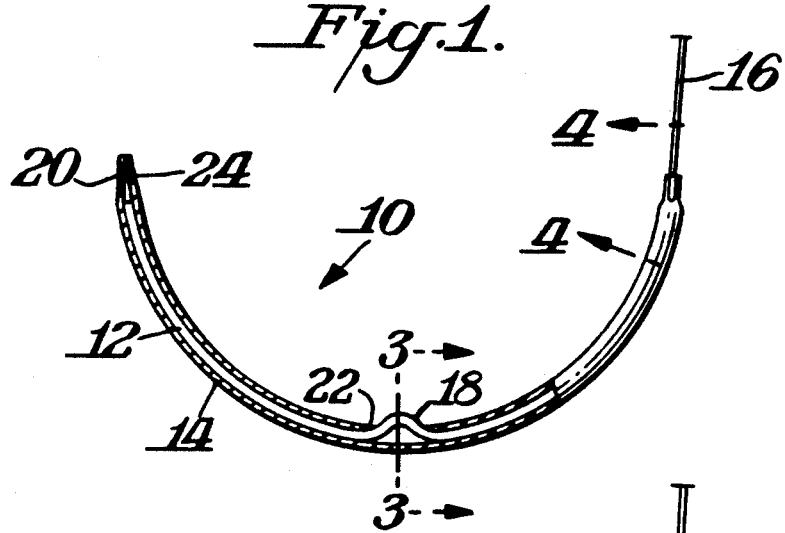
FIG. 1 is a side elevational view of the suturing assembly having a portion broken away.

A suturing assembly 10 shown in FIG. 1 includes a surgical needle 12, casing 14 and suture 16.

The surgical needle 12 includes a stem along a generally elongated longitudinal axis, defining the main body of the surgical needle. A portion of the stem is laterally offset in the form of an arch or hump 18. The stem has a generally uniform cross-sectional area throughout the entire length thereof.

The distal portion 20 of the needle 12 defines a tapered portion whose cross-sectional area decreases progressively toward a pointed or sharpened end of the needle.

The proximal portion of the needle may be of any configuration. It may be a blunt end of the needle of the same cross-sectional area as the stem, or it may be tapered. In one embodiment of the invention, the proximal end defines a suture-mounting portion by which a suture can be directly attached to the surgical needle. Suture-mounting can be made by any conventional means, such as by defining a blind hole, i.e., a cylindrical recess, extending from a proximal end face of the suture needle along the axis thereof. The length of the suture-mounting portion is generally equal to or slightly greater than the length of the hole. A suture is inserted into the hole and then the suture-mounting portion is crimped, i.e., deformed or compressed, to hold the suture. Alternatively, the suture can be secured by the addition of a cement material to such blind hole, as shown in, for example, U.S. Pat. No. 1,558,037. Reference is also made to U.S. Pat. Nos. 2,928,395 and 3,394,704, which disclose, respectively, adhesives and bonding agents. The hole in the proximal end face of the needle can also be prepared by means such as that disclosed, or similar to that disclosed, in U.S. Pat. No. 4,910,377 to Matsutani et. al. The suture can also be attached to the needle by means as disclosed, or similar to that disclosed, in U.S. Pat. No. 4,901,722 to Noguchi, in U.S. Pat. No. 4,890,614 to Kawada et. al., in U.S. Pat. No. 4,805,292 to Noguchi, or in U.S. Pat. No. 5,102,418 to Granger.

The surgical needle itself can be made by cold-drawing a wire of stainless steel into a required diameter, with its crystal grains arranged into a fiber-like structure. The wire is cut into a suitable length, and, if a suture-mounting is desired, the suture-mounting portion is prepared as by forming a blind hole, i.e., a cylindrical recess, in the proximal face of the cut stock. The distal end is ground or machined on a lathe, or otherwise reduced in diameter by any conventional means, to form the tapered penetrating point portion. The needle is then bent to provide the hump in the stem. If desired, the needle can then be subjected to heat or surface treatment. A suture can then also be inserted into the blind hole in the proximal face, and the suture-mounting portion can be deformed or compressed so as to fixedly secure the suture thereto.

Figure 3:
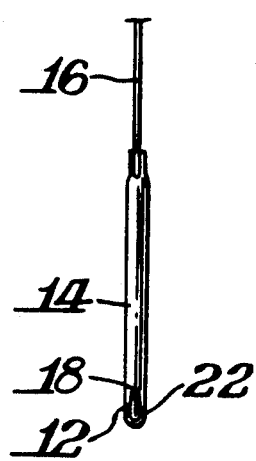
FIG. 3 is a cross sectional view taken along line 3—3 of FIG. 1.

The needle is within a casing or sheath 14. The casing is hollow and elongated in a longitudinal direction, and has an aperture 22, as more clearly shown in FIG. 3. The needle and the casing are in a coaxial relationship so that the hump 18 of the needle 12 protrudes through the aperture 22, as shown in FIG. 3. The proximal ends of the surgical needle and the casing are in a relationship such that no lateral movement of the surgical needle is possible. For example, a portion of the proximal end of the casing can be crimped around and unto the proximal end of the needle. The parameter is important in that it is desirable that, when the hump of the surgical needle is deformed, the needle is extended only in the distal direction so that it will project through the distal opening of the casing.

The casing should be in a close relationship to the surgical needle, but such that the portion of the surgical needle distal to the hump can move laterally within the casing. The interior of the casing in that distal portion can be coated with a physiologically-acceptable lubricant, e.g., Teflon ® (PTFE), to ease the movement of the surgical needle within the casing. The distal open end of the casing 24 is shaped to conform to the geometry of the distal end of the surgical needle (i.e., tapered point, cutting, blunt point, and the like). Generally, the distal point of the casing 24 is preferably beveled so that when the surgical needle 12 is extended through the distal opening of the casing 24, as showing in FIG. 2, the needle and the casing will form a substantially uniform tapered surface. The opening 24 may preferably be slightly rounded to avoid any potential sharp edge which itself may cut or puncture the operating room personnel, but not sufficiently rounded to create a ledge-effect when the assembly is passed through tissue. At rest, as shown in FIG. 1, the casing extends just beyond the sharpened distal point of the needle so that the point cannot puncture the skin of anyone accidentally touching the open end of the suturing assembly.

The hump 18 of the surgical needle 12 is such that at rest it will protrude only minimally through the aperture 22, so that the hump will not enlarge the hole in the tissue when the assembly is passed through the tissue to be sutured. The lateral height of the hump should be only that sufficient to permit the sharpened distal point of the needle to project through the distal casing opening. The size and geometry of the hump 18 are selected so that the elongation of the needle is sufficient to cause the sharpened point of the needle to project from the casing 14, and desirably will form a seal between the casing and the emerged needle. The seal need not be tight, the object being to provide a relatively smooth path from needle point to casing to avoid unnecessary tearing or enlargement of the needle hole.

The casing can be made and be formed to encase the surgical needle by any conventional means. One method would be to make the casing in two sections each section running the full length of the casing and having half of the aperture at the desired point. The lubricant would be applied to the forward part of the casing, the needle placed in one of the sections, the other section placed on the top (the aperture openings gripping the hump to provide proper centering), the suture inserted, the suture, needle, sheath crimped together and the sides of the sheath sealed as by brazing or welding. Alternatively, the casing can be made in one piece, but opened along the longitudinal axis. The surgical needle and suture would then be located in the casing, and the casing would be closed by crimping or other conventional means. The casing may also be preformed and the surgical needle inserted from the proximal end of the casing by deforming the hump of the needle until the needle hump is within the casing, and then advancing the needle until the hump is immediately coaxial with the aperture, at which point the hump of the needle will pop into place by protruding through the aperture.

The casing 14 may have annular channels or ribs (not shown) grooved into the body portion extending along the longitudinal axis adapted to accommodate better stability and control by limiting twisting of the assembly.

The suture material 16 can be of any conventional material, including any of the wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

The suture can be secured to the casing by crimping or by cement or other adhesive. The suture can also be secured to the proximal end of the needle, as previously described, or both to the needle and the casing.

Whether the suture is attached to the surgical needle, casing or both, the attachment can be either standard, i.e., the suture is securely attached and is not intended to be separable therefrom, except by cutting or severing the suture, or be removable or detachable, i.e., be separable in response to a force exerted by the surgeon. Minimum acceptable forces required to separate a needle from a suture (for various suture sizes) are set forth in the United States Pharmacopeia (USP).

The suture attached to the surgical needle, casing or both by crimping can be either a standard attachment, or can be detachably secured by means as disclosed, or similar to that disclosed, in U.S. Pat. Nos. 3,890,975 and 3,980,177. The many known means of detachably securing a suture to a surgical needle, as well as standard attachment means, are disclosed in U.S. Pat. No. 5,102,418 to Granger et. al.

Figure 4:
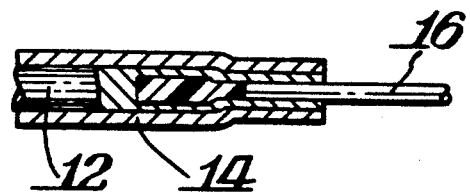
FIG. 4 is a cross-sectional view taken along line 4—4 of FIG. 1.

Both a preferred attachment of the suture and preferred formation of the proximal end of the suturing assembly is shown in FIG. 4. The suture 16 is inserted into a blind hole in the proximal face of the surgical needle 12. Thereafter the proximal ends of the casing 14 and the needle 12 are crimped. As a result, the suture 16 is attached to the assembly, and the needle 12 is so fixed in the casing 14 that the needle will not move in the proximal direction when the hump of the needle is deformed.

As shown in FIG. 1 and FIG. 3, the hump 18 of surgical needle 12 protrudes slightly through the aperture 22 in the casing 14 at approximately the middle of suture assembly 10. However, the hump and aperture assembly can be anywhere along the longitudinal axis considering the distal length necessary to penetrate the tissue and the maximum bending moment of the curved assembly. For a curved needle the surgeon works with the interior or concave portion up. For this reason, in the case of a curved needle the hump 18 is preferably placed on this side of the needle as shown in FIGS. 1-3.

Figure 2:
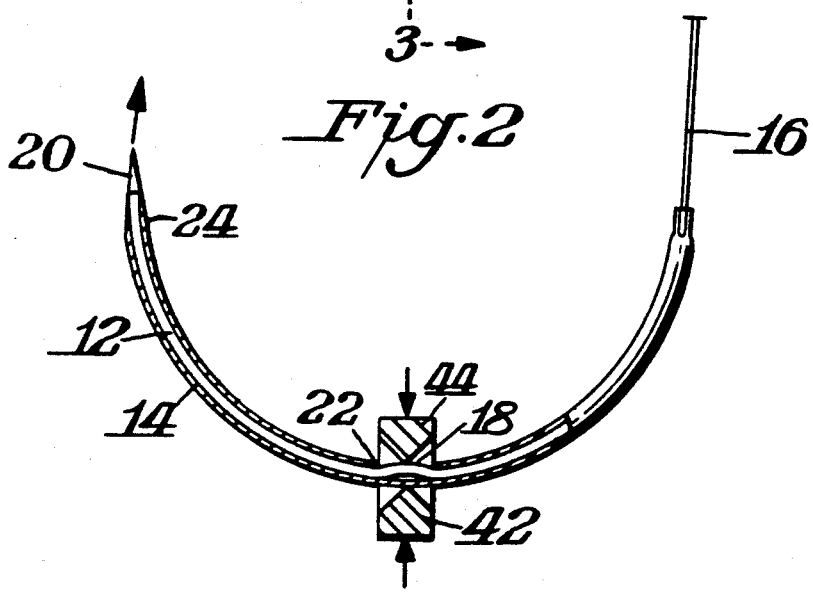
FIG. 2 is a side elevational view of the suturing assembly showing the surgical needle extended beyond its casing as the result of a needle holder compressing the arch-shaped hump shown in FIG. 1.

As shown in FIGS. 1 and 2, the suturing assembly, including the surgical needle and casing, is curved. However, the suturing assembly can be of any other configuration, so long as the surgical needle can move along the longitudinal axis of the casing. The assembly, for example, can be in the form of a ¼circle, ⅜circle, ½curve, ½circle, ⅝circle, or straight. The surgical needle distal points can be taper point, taper cut, reverse cutting, precision point, spatula-type, and the like.

The surgical needle and casing may be made of medically-acceptable martensite-type stainless steel or precipitation hardened stainless steel. A specific nickel titanium martensitic steel disclosed in U.S. Pat. No. 5,000,912 to Bendel et. al. (Ethicon, Inc.) is cited. The needle should provide the sharp points or edges needed in a surgical needle and to provide the bending and return to original shape required for the assembly to work as described. Desirably the casing is made of a medically acceptable material such as a stainless steel which will provide sufficient strength when secured to the needle at the suture end (as by crimping) to prevent the needle from breaking out at that end when the hump is depressed as described. It should also provide sufficient rigidity so that when the hump is deformed, the casing is not deformed so as to prevent the retraction of the needle point when the deforming force is released. The choice of material depends to a large extent on the manufacturing process and the choice of suture-mounting. For example, it is reported that it is exceedingly difficult to drill Series 300 stainless steel to make a blind hold for a suture, which required laser drilling, and difficult to crimp the steel in a consistent and reliable manner. Series 300 stainless steel, however, has substantial advantages in strength and ductility compared to conventional Series 400 stainless steel. The components, particularly the casing, may also be made of medically-acceptable, high-durometer polymeric material.

The suture assembly will preferably be sterilized and packaged in a sterile, ready-to-use package by the same means as conventionally used for delivery of surgical devices.

Figure 5:
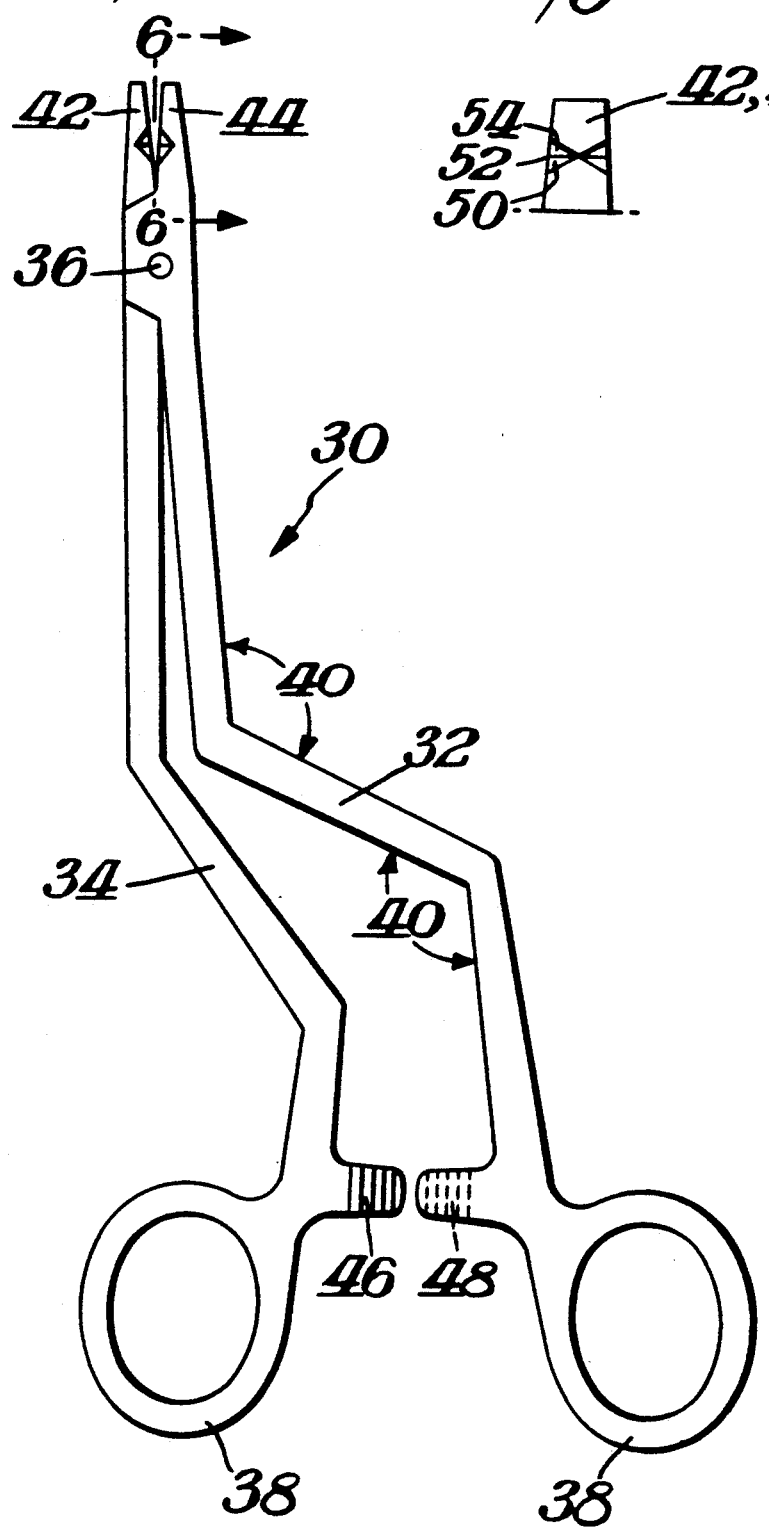
FIG. 5 is a plan view showing a needlé holder.
Figure 6:
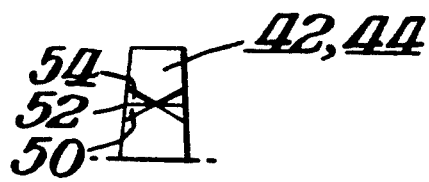
FIG. 6 is a cross-sectional view along line 6—6 of FIG. 5 showing the jaw of the needle holder shown in FIG. 5.

The suturing assembly is preferably manipulated by means of a driver designed for use with the suturing assembly. One form of such a driver is shown in FIG. 5. The driver 30 comprises a pair of non-crossing pivoted arms 32 and 34 which rotate at axis 36 in the same plane. The arms are offset, allowing the surgeon to place the suturing assembly without obstruction and with ease into remote crease and crevices of the body. By decreasing angles 40 of the arm 32 and maintaining relatively short the length of the distal driver jaws 42 and 44, substantial pressure may be applied by the jaws. The driver contains a conventional ratchet mechanism 46 and 48, providing for preferably five locked positions. The proximal portions of the arms 38 have a gripping shape for use when the driver is held by a human hand. As shown in FIG. 6, jaws 42, 44 preferably have grasp surfaces in the form of three shallow serations or grooves 50,52 and 54, cut into the surface portion thereof to match or approximately match the outer surface of the casing. Groove 52 is cut transversely to the plane of the jaws, and grooves 50 and 54 are cut in the form of an X. The grooves 50 and 54 permit the driver to hold the suturing assembly at an angle. The grasp surfaces of distal jaws 42 and 44 are disposed parallel to each other.

In use, the nurse opens the sterile pouch containing the suture assembly and grasps the assembly 10 with a needle holder or driver 30 engaging the hump 18 in the first locked position. The distal jaws of the driver are held respectively against the needle hump and the casing opposite the hump, thereby stably grasping or holding the suturing assembly. The drivers jaws 42 and 44 will securely hold the suturing assembly but not deform the hump. The driver 30 gripping the assembly as described is then handed to the surgeon. The needle has sufficient rigidity so that the force exerted by the driver when in the first locked position does not deform the hump sufficiently to cause the needle point to project from the open end of the casing. The surgeon now applies full locking force to the driver. This force significantly flattens and clamps the hump and elongates the needle, i.e., the hump of the surgical needle is deformed so that the surgical needle is straightened in a longitudinal direction as shown in FIG. 3. As a consequence, the distal sharpened point of the surgical needle is advanced distally through the distal opening of the casing. The needle is preferably prevented from elongating at the suture end by reason of the needle—casing seal at the end so that the elongation occurs at the distal end of the assembly. The suturing assembly is then directed to pierce the tissue to the desired depth. After the assembly is inserted, the surgeon releases the locking force. The hump pops back into the aperture, and the assembly is pulled through by hand or by the same or another needleholder. The surgeon replaces the driver to grip the assembly at the aperture and the process is repeated.

FIG. 7 illustrates a suturing assembly 10A having a surgical needle 12 within a casing 14. The casing 14 is hollow and elongated in a longitudinal direction and has an elongated aperture 62, as described before, and the pin 60 that is attached to the needle is within the aperture. Preferably, the pin protrudes through the aperture.

The casing 14 has a suture material 16 attached to the needle and extending from one proximal end of the casing. The suture material and its attachment to the needle have been earlier described in the detailed description.

The opposite distal end of the casing has a beveled opening 24 that corresponds to the bevel of the needle 20, when the needle is extended to its operative position as shown in FIG. 11.

FIG. 8 illustrates the surgical pliers 30A comprising handles 38 attached to a pair of non-crossing pivoted arms 32 and 34 which rotate at axis 36 in the same plane. Extending longitudinally away from pivot axis 36 are jaws 42A and 44A respectively attached to arms 32 and 34.

Jaw 42A and 44A have concave recesses 66 and 64 respectively designed to engage and conform to the needle casing 14. Rachet mechanism 46 and 48 on handles 34 and 32 can be interlocked in any of five positions to maintain the desired closure pressure between jaws 42A and 44A.

FIGS. 8-11 show jaw 44A and details of slide assembly 58 that comprises a window 68 to allow jaws and slide assembly to be properly positioned with elongated slot 62 and pin 60 on the needle during clamping.

Located in the window area is a slide 70 that has a socket 72 that telescopically engages pin 60 attached to the needle 12.

FIG. 10 also shows pin engaging socket 72 is within the perimeter of elongated slot 62, which permits the needle to be extended longitudinally.

FIGS. 9 and 10 show the end portions of the slide which are movably recessed in dado slots 74. Springs 76 within the confines of the dado recesses bias the slide in a retracted position to facilitate socket 62 engagement with needle pin 60. The jaws 42A and 44A also are rigidly clamped to the casing to allow for the extrusion of the needle tip for suturing.

FIG. 11 shows the needle point 20 extended longitudinally beyond the tapered distal end of the casing for insertion into the tissue to be sutured. FIG. 9 shows cables 78 attached to slide 70, these cables pass through openings 79 in jaw 44A and down through eyelets 80 on the surgical plier body to a pull ring 82. A downward pull on the ring 82 is transmitted back via the cables to the slide causing the slide 70 to move forward in dados 74 while compressing the springs 76.

As a direct result of the slides forward movement and the engagement of the slide socket with the needle pin the needle has been urged longitudinally in the casing 14 so the needle point is in operative position for suturing.

The extended needle pierces the tissue to the desired depth at reaching the desired depth the surgeon releases the cable eyelet. The springs 76 bias the slide 70 to its inoperative position thereby the needle is then retracted into the casing because of the slide socket direct engagement with the needle pin. The next suture stitch position is arrived at as previously described, i.e., the slide is urged forward and the needle is extended beyond the casing.

I claim:
1. A suturing assembly comprising:
a) a casing comprising
  i) an elongated hollow shaft having a generally longitudinal axis,
  ii) an aperture along a portion of the longitudinal axis, and
  iii) an opening terminating the casing at the distal end;
b) a surgical needle comprising
  i) a stem along a generally elongated longitudinal axis having a pin along a portion thereof perpendicularly offset from the longitudinal axis, and
  ii) a sharpened distal point terminating the stem in one direction;
c) said surgical needle located within said casing whereby
  i) the longitudinal axis of said surgical needle and casing are disposed in a substantially coaxial relationship,
  ii) with the pin of said surgical needle disposed within the aperture of said casing,
  iii) the sharpened distal point of the said surgical needle being disposed proximal to the opening of the distal end of said casing at rest and capable of being projected through the said distal opening of said casing upon the application of sliding force to the said pin of said surgical needle, and
  iv) whereby the said surgical needle and said casing can be manipulated as a unit upon the application of manipulative force thereto; and
d) a suture having an end portion thereof inserted into and fixed to the needle, casing or both.

2. The assembly of claim 1 wherein the suture is detachably attached to the surgical needle.

3. The assembly of claim 1 wherein the suture is detachably attached to the surgical casing.

4. The assembly of claim 1 wherein the distal end of the casing conforms to the shape to the distal end of the surgical needle.

5. The assembly of claim 1 wherein the distal end of the casing is beveled.

6. A suturing method comprising
I) grasping a suturing assembly generally comprising in a rest position
  a) a casing comprising
    i) an elongated hollow shaft having a generally longitudinal axis,
    ii) an aperture along a portion of the longitudinal axis, and
    iii) an opening terminating the casing at the distal end;
  b) a surgical needle comprising
    i) a stem along a generally elongated longitudinal axis having a pin along a portion thereof perpendicularly offset from the longitudinal axis, and
    ii) a sharpened distal point terminating the stem in one direction;

c) said surgical needle located within said casing thereby
   i) the longitudinal axis of said surgical needle and casing are disposed of in a substantially coaxial relationship,
   ii) with the pin of said surgical needle disposed within the aperture of said casing, and
   iii) the sharpened distal point of the said surgical needle being disposed proximal to the opening of the distal end of said casing, and
d) a suture having an end portion thereof inserted into and fixed to the needle, casing or both;

II) sliding the pin and the needle stem in a distal direction so as to extend the longitudinal length of the surgical needle within the casing until the sharpened distal point of the needle projects through the distal opening of the casing;

III) piercing the material to be sutured.

7. The suturing method of claim 6, which includes the steps of retracting the sliding force on the pin so that the needle returns to a rest position; and advancing the suturing assembly as a unit through the material to be sutured.

* * * * *